(12) United States Patent
Villette

(10) Patent No.: US 8,273,062 B2
(45) Date of Patent: Sep. 25, 2012

(54) INJECTION NEEDLE

(76) Inventor: Alain Villette, St. Pierre les Echaubrognes (FR)

( * ) Notice: Subject to any disclaimer, the term of this patent is extended or adjusted under 35 U.S.C. 154(b) by 0 days.

(21) Appl. No.: 12/604,546

(22) Filed: Oct. 23, 2009

(65) Prior Publication Data

US 2010/0106104 A1    Apr. 29, 2010

(30) Foreign Application Priority Data

Oct. 28, 2008 (FR) .................................. 08 57306

(51) Int. Cl.
*A61M 5/32*      (2006.01)
(52) U.S. Cl. ......... 604/272; 604/264; 604/273; 604/274
(58) Field of Classification Search ................. 604/264, 604/272–274; 606/80
See application file for complete search history.

(56) References Cited

U.S. PATENT DOCUMENTS

| | | | | |
|---|---|---|---|---|
| 4,490,139 A | * | 12/1984 | Huizenga et al. | 604/57 |
| 5,354,537 A | * | 10/1994 | Moreno | 422/512 |
| 5,575,780 A | * | 11/1996 | Saito | 604/272 |
| 5,968,022 A | * | 10/1999 | Saito | 604/272 |
| 7,591,807 B2 | * | 9/2009 | Villette | 604/272 |

FOREIGN PATENT DOCUMENTS

DE    10 2005 027 147 A1    12/2006
FR         2 540 385 A1    8/1984

* cited by examiner

*Primary Examiner* — Bhisma Mehta
*Assistant Examiner* — Larry R Wilson
(74) *Attorney, Agent, or Firm* — Leydig, Voit & Mayer, Ltd.

(57) ABSTRACT

The invention relates to an injection needle for injecting a pharmaceutical product into a human or animal body. The needle comprises a tubular body with an end for penetrating into a human or animal body, and having a main bevel and a secondary bevel forming a tip of the needle. The secondary bevel is positioned opposite the main bevel and forms, with the main bevel, a single cutting edge oblique to the longitudinal axis of the tubular body. The cutting edge extends on both sides of a middle plane of the main bevel that passes through the longitudinal axis of the tubular body.

3 Claims, 2 Drawing Sheets

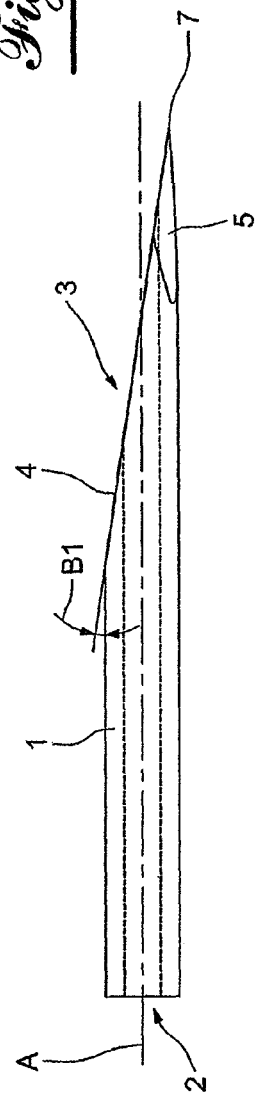
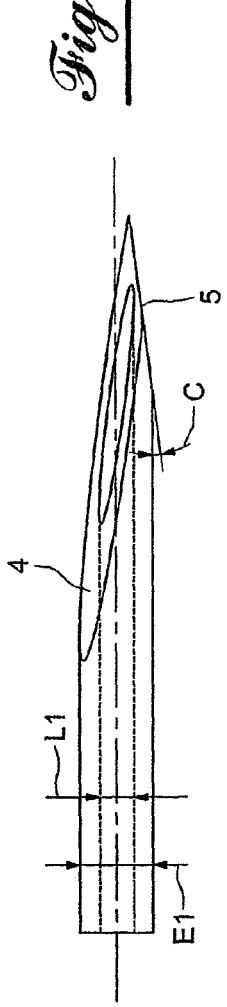
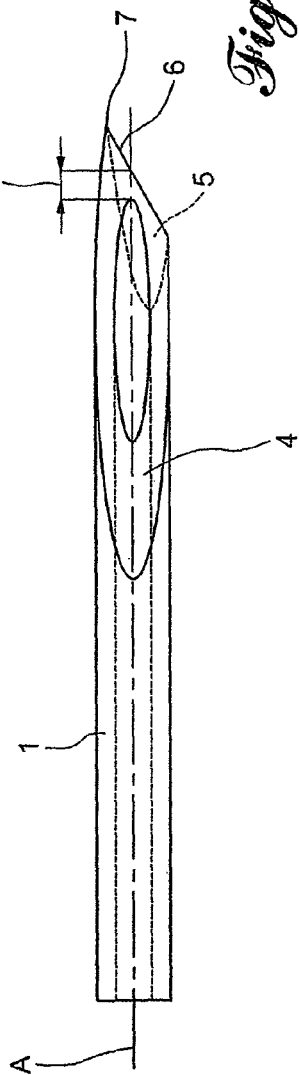
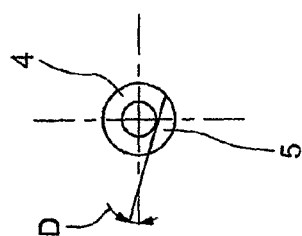

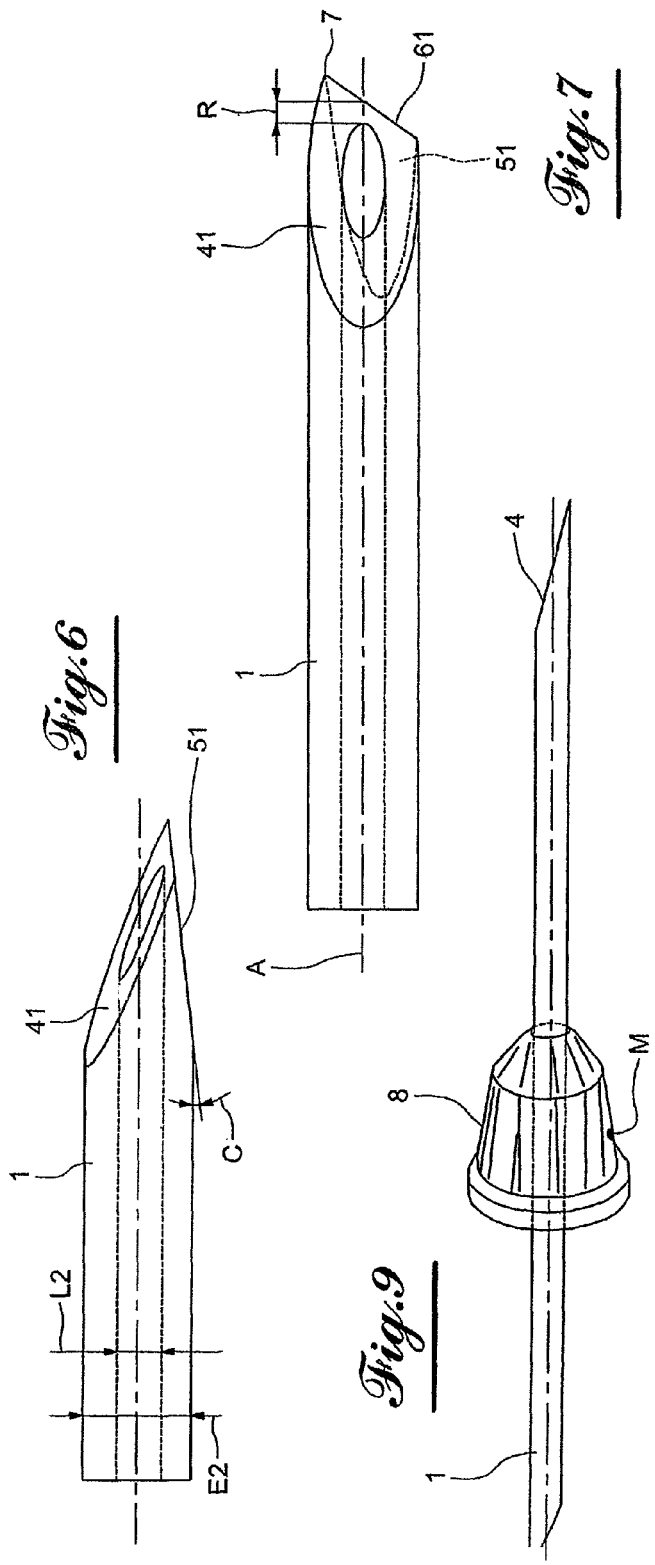

INJECTION NEEDLE

FIELD OF THE INVENTION

The invention relates to an injection needle for injecting a pharmaceutical product in human or animal body tissue.

BACKGROUND

During certain surgical operations and during dental care, a local anesthetic has to be administered to the patient. This anesthesia is limited to the targeted region and in the case of dental care, should be limited to the tooth or teeth to be treated. The anesthetic product is generally administered by injection into the tissues to be anesthetized.

During dermatological treatments in humans or in animals, it is sometimes useful to have a needle designed in order to perform an injection in a safer and less painful way.

During dental treatments, the injection of an anesthetic product is usually performed in the gums in order to produce effects in the peripheral soft tissues. It is then useful to have a needle available with which the considered anesthesia location may be reached as accurately as possible in order to be able to limit the amount of anesthetic product to be administered.

However, and independently of the annoyances which this represents for the patient, the effectiveness of the anesthesia is not always optimum, since the anesthetic product is partly distributed at a distance from the tooth to be treated instead of remaining concentrated therein. Further, the injection needle is often deviated, since it deforms upon penetrating into the tissues, especially in soft tissues.

Indeed, the needles according to the present invention are mainly intended for administering anesthetic products, but moreover also for other applications, for example dermatological applications, where the question is of depositing a pharmaceutical product in a well-specified location of the human or animal body.

Among the different anesthesia techniques, the present invention is more particularly of interest for intraligamentary anesthesia and troncular anesthesia as practiced in dental surgery.

Intraligamentary anesthesia consists of injecting an anesthetic product into the ligaments surrounding the tooth to be treated. The problem posed by intraligamentary anesthesia with conventional needles is the difficulty experienced for having the needle penetrate sufficiently deeply into the ligament. This very often causes even with the finest needles, leaks of anesthetic. In order to find a remedy to this problem, the practitioner tries to push in his/her needle more deeply and most of the time it bends. This imposes a change of needle and a new prick.

Troncular anesthesia is an anesthesia technique of the lower dental nerve before its entry into the dental channel. During the penetration of a needle into a soft tissue, particularly during troncular anesthesias or locoregional anesthesias, the needle is pushed in quite deeply. During its penetration, the conventional needle deforms and follows a curved trajectory which causes the injection to be never exactly performed at the contemplated location. This is a non-negligible failure factor. To find a remedy to this, several solutions have been proposed. It should be known that most dental needles used are of a diameter of 0.4 or 0.5 mm. First, the diameter of the needle needs to be increased in order to increase its rigidity. It is recommended to preferentially use the diameter of 0.51 mm. Conventionally, the inner diameter of this needle is 0.25 mm. It is recommended to use the bi-rotational insertion technique (BRIT), which consists of rotating the needle during the penetration alternately by one half-turn in one direction or the other, this so that the effects of the deviation are canceled out. This handling is rather difficult to perform and only automatic injection syringes allow this.

SUMMARY OF THE INVENTION

The object of the invention is to propose an injection needle in order to administer pharmaceutical products, which finds a remedy to the drawbacks described hereinbefore.

The object of the invention is achieved with an injection needle for injecting a pharmaceutical product into a human or animal body, the needle comprising a tubular body having two opposite ends, one first end of which intended to be connected to product supply means and a second end intended to penetrate into the human or animal body, the second end being provided with a main bevel and a secondary bevel forming a tip of the needle.

According to the invention, the secondary bevel is positioned opposite to the main bevel and forms with the main bevel a single cutting edge, oblique relatively to a longitudinal axis of the tubular body, the cutting edge extending on either side of a middle plane of the main bevel passing through the longitudinal axis of the tubular body.

By means of the opposite positioning of the secondary bevel relatively to the main bevel and the extent of the cutting edge on either side of a middle plane of the main bevel passing through the longitudinal axis of the tubular body, the front end of the needle, as seen in the direction of penetration of the needle into a body, is formed so as to subject the needle to approximately opposite forces which are mutually reduced. Consequently, the deviation of the needle is at the very least reduced.

This positive effect of the injection needle according to the invention may further be improved by giving to the needle at least one of the features hereafter, considered separately or according to any technically possible combination:

the secondary bevel forms with the longitudinal axis of the tubular body an angle of less than 10 degrees;

the main bevel forms with the longitudinal axis of the tubular body an angle comprised between 5 degrees and 25 degrees;

the main bevel forms with the longitudinal axis of the tubular body an angle comprised between 5 degrees and 10 degrees;

the main bevel and the secondary bevel enclose between them an angle comprised between 15 degrees and 30 degrees;

the tubular body has an inner diameter less than the standardized values for the different needle calibers;

the needle is provided with a positioning marking, positioned relatively to the longitudinal axis of the needle, opposite to the main bevel.

BRIEF DESCRIPTION OF DRAWING FIGURES

Other features and advantages of the present invention will become apparent from the description hereafter of two constitutive needles of exemplary embodiments. The description is made with reference to the drawings wherein:

FIG. 1 illustrates a first injection needle according to the invention in a side view with view on the secondary bevel, FIG. 2 illustrates the first needle in a side view with view on the main bevel, FIG. 3 illustrates the first needle with a top view on the main bevel, FIG. 4 illustrates the first needle in an axial view on both bevels, FIG. 5 illustrates a second injection needle according to the invention in a side view with view on the secondary bevel, FIG. 6 illustrates the second needle in a side view with view on the main bevel, FIG. 7 illustrates the second needle with a top view on the main bevel, FIG. 8 illustrates the second needle with an axial view on both bevels, and FIG. 9 illustrates an injection needle with a positioning marking.

DETAILED DESCRIPTION

FIGS. 1-4 illustrate an injection needle for intraligamentary anesthesia. The needle comprises a tubular body 1 with a longitudinal axis A and two opposite ends 2, 3, one first end 2 of which is conformed in order to be connected to the product supply means, for example to a syringe or a flexible conduit which itself is connected to a cylinder or any other type of container, or to an automatic apparatus conformed in order to administer a pharmaceutical product in a programmable way.

The second end 3, which is intended to penetrate into a human or animal body, is provided with a main bevel 4 and a secondary bevel 5 forming both a single cutting edge 6 and a tip 7 of the needle.

The tubular body 1 of the injection needle is a substantially hollow cylindrical body and axisymmetrical around the longitudinal axis A. The tubular body 1 thus has an outer diameter E1 and an inner diameter L1. When the outer diameter E1 indicates the caliber of the injection needle, the inner diameter L1 indicates the size of the lumen of the tubular body 1 through which the pharmaceutical product should be able to pass during an injection.

The injection needles used in dental surgery for intraligamentary anesthesia are made from tubes having an outer diameter of 0.3 mm. According to the invention, such a tube is provided, at the end intended to penetrate into a human or animal body, with a main bevel 4 and a secondary device 5 positioned opposite to each other and with a relatively small angle D between both bevels. In this way, the intersection between both bevels 4, 5 results in an oblique cutting edge 6 relatively to the longitudinal axis A of the tubular body 1 of the needle. The orientation of the cutting edge 6 substantially depends on the relative orientation of both bevels relatively to each other, the orientation relatively to the axis A of the tubular body 1 is more and more away from a perpendicular arrangement relatively to the axis A as the angle D between the bevels increases gradually.

However, the orientation of the cutting edge 6 also depends on the angle which each of the two bevels forms with the longitudinal axis A of the tubular body 1. In the case of injection needles for intraligamentary anesthesia, the angle B between the main bevel 4 and the longitudinal axis A and the angle C between the secondary bevel 5 and the longitudinal axis A are at least approximately equal and as small as possible, considering technical manufacturing constraints. By giving both angles B and C values of less than 10° relatively to the longitudinal axis A, very flat needles are made which may be deeply inserted into a ligament.

At the same time, the small angles between each of the two bevels 4, 5 and the longitudinal axis A, and more particularly the small angle C between the secondary bevel 5 and the longitudinal axis A, are only possible by the use of a special tube having a thicker wall than this is the case for tubes according to the ISO 9626 standard which for example sets the following values:

| Theoretical dimension | | Outer diameter (mm) | | Inner | Thickness of the wall (mm) | |
|---|---|---|---|---|---|---|
| (mm) | Caliber | min | max | diameter (mm) | min | Max |
| 0.3 | 30 | 0.298 | 0.320 | 0.133 | 0.083 | 0.094 |
| 0.5 | 25 | 0.500 | 0.530 | 0.232 | 0.134 | 0.149 |

By using, for making needles according to the invention, a tube having a thicker wall because it has a reduced inner diameter L1 relatively to that of standardized needles, i.e. by decreasing the diameter of the lumen of the needle, the secondary bevel 5 may be brought closer to the longitudinal axis A of the tubular body 1, which decreases the length of the lumen at the end 3 of the needle.

In this way, injection needles may be obtained having the following characteristics for example:

| Theoretical dimension | | Outer diameter (mm) | | Inner | Thickness of the wall (mm) | |
|---|---|---|---|---|---|---|
| (mm) | Caliber | min | max | diameter (mm) | min | Max |
| 0.3 | 30 | 0.298 | 0.320 | 0.110 | 0.094 | 0.110 |
| 0.5 | 25 | 0.500 | 0.530 | 0.200 | 0.150 | 0.165 |

Further, the angle C between the secondary bevel 5 and the longitudinal axis A may be reduced relatively to conventional needles. A similar idea applies to the orientation of the main bevel 4 and of the angle B1 which it forms with the longitudinal axis A. In the exemplary embodiment illustrated in FIGS. 1-4, both angles B1 and C are equal with the same tolerance and have numerical values of 7°±1°.

The injection needle according to the invention, conformed in order to be able to be used in intraligamentary anesthesia, mainly benefits from two advantages. First of all, by making the needle with a blade-shaped end, it is possible to have it penetrate more deeply into a tissue, therefore suppressing leaks during the injection, and then exposing it as less as possible to transverse components of the resistance forces which the needle encounters when penetrating more and more deeply into the tissue. Moreover, by using a thicker-walled needle, the person or the animal to be treated may benefit from advantages of a more rigid tube and the needle is therefore less subject to deformation, notably flexure, a main source of deviation of conventional needles.

To summarize, the needles according to the invention are improved relatively to conventional needles under two different aspects, each of which contributes independently of each other to greater linearity of the penetration path. At the same time, both of these advantages add up and are amplified.

In order to fully make the most of the advantages provided by the present invention, the needles according to the invention are advantageously provided, on a base 8 of the needle in which the tubular body is housed, with a positioning marking M visible in FIG. 9. The marking is located on the back of the needle relatively to the main bevel 4. This allows the practitioner to know that the main bevel 4 of the needle is actually parallel to the mucosa.

When the injection needle according to the invention is made for applications in troncular anesthesia, i.e. for depositing a pharmaceutical product and notably an anesthetic product close to a nerve trunk, needles of caliber 25, i.e. having an outer diameter of 0.5 mm, are conventionally used. However, in order to have these needles benefit from the arrangements of the invention, they are made from tubes having an inner diameter of the order of only 0.20 mm. The result of this is needles with thicker walls than the walls of standardized needles. This increase in the thickness of the wall of the needle first allows an increase in its rigidity and thus a reduction in its flexure upon penetrating a tissue. Next, with this increase in the thickness of the wall the secondary bevel may be brought closer to the longitudinal axis A of the tubular body 1 without penetrating the lumen.

Thus, for the injection needle made according to the second exemplary embodiment illustrated in FIGS. 5-8, the same basic arrangements as those described in connection with the first exemplary embodiment, are again found.

However, because of a larger caliber E2 of the needle according to the second exemplary embodiment, relatively to the caliber E1 of the needle of the first exemplary embodiment, and because of an inner diameter L2 proportionally less large than the inner diameter L1 of the needles of the first exemplary embodiment, the angle of the main bevel 41 of the needle according to the second exemplary embodiment cannot be as small as the angle of the main bevel according to the first exemplary embodiment. Thus, the angle B2 which the main bevel 41 forms with the longitudinal axis A is of the order of 20°-25°, for example 21°±1°.

Unlike this, the angle C which the secondary bevel 51 forms with the longitudinal axis A of the conduit 1, is equal to that of the needles of the first exemplary embodiment, i.e. less than 10°, preferably 7°±1°. Thus, both for the secondary bevel 5 according to the first exemplary embodiment and for the secondary bevel 51 according to the second exemplary embodiment, an angle C formed with the longitudinal axis A ranging up to 6° may be contemplated.

Although the main bevel and the secondary bevel of the needle according to the second exemplary embodiment do not have angles as small as according to the first exemplary embodiment, the end of the needle is nevertheless subject to almost equivalent opposite forces, and notably with small transverse components, which significantly reduces the risk of deviation of the needle upon penetrating the tissues of a human or animal body.

The invention claimed is:

1. An injection needle for injecting a pharmaceutical product into animal tissue, the needle comprising a tubular body having a longitudinal axis and a tissue penetrating end, the tissue penetrating end consisting of
   a main bevel oblique to the longitudinal axis,
   a secondary bevel positioned opposite the main bevel, and
   a tip at which the main bevel and the secondary bevel intersect, the tip having a single linear cutting edge that is oblique to the longitudinal axis and extends on both sides of a medial plane of the main bevel that passes through the longitudinal axis, wherein
      the secondary bevel forms a first angle with the longitudinal axis that is less than ten degrees, and
      the main bevel and the secondary bevel form, between them, a second angle within a range from 15 degrees to 30 degrees.

2. The needle according to claim 1 wherein the main bevel forms a third angle with the longitudinal axis within a range from 5 degrees to 10 degrees.

3. The needle according to claim 1 wherein the main bevel forms a third angle with the longitudinal axis within a range from 5 degrees to 25 degrees.

* * * * *